United States Patent [19]
Wiesemann et al.

[11] Patent Number: 5,728,059
[45] Date of Patent: Mar. 17, 1998

[54] SLIT SLEEVE WRIST SUPPORT

[75] Inventors: Sidney Michael Wiesemann, Cincinnati; Sherry Ann Hinds, Goshen, both of Ohio

[73] Assignee: Beiersdorf AG, Hamburg, Germany

[21] Appl. No.: 561,723

[22] Filed: Nov. 22, 1995

[51] Int. Cl.[6] .................. A61F 5/04; A61F 13/00
[52] U.S. Cl. .................. 602/64; 602/21; 128/878
[58] Field of Search .............. 473/62, 63; 128/878, 128/879; 602/20, 21, 22

[56] References Cited

U.S. PATENT DOCUMENTS

| | | |
|---|---|---|
| 3,327,703 | 6/1967 | Gamm . |
| 4,854,309 | 8/1989 | Elsey et al. . |
| 4,883,073 | 11/1989 | Aziz . |
| 4,944,766 | 7/1990 | Williams . |
| 5,014,689 | 5/1991 | Meunchen et al. . |

FOREIGN PATENT DOCUMENTS

| | | |
|---|---|---|
| 56828 | 11/1989 | Australia . |
| 0162610 | 11/1985 | European Pat. Off. . |

*Primary Examiner*—Richard J. Apley
*Assistant Examiner*—Kim M. Lee
*Attorney, Agent, or Firm*—Sprung Kramer Schaefer & Briscoe

[57] ABSTRACT

A slit sleeve wrist support includes a sheet of elastic fabric that is wrapped around the wrist and hand and fastened with hook and loop fastener straps. The sheet has a proximal edge to be positioned around the arm and a distal edge to be positioned at the hand near the fingers. Each of the lateral edges is formed with a inward curved space near the distal end to accommodate the user's thumb. The curvature at each lateral edge defines opposed, laterally extending thumb tabs at the distal end of the sheet. Two elongated pockets are sewn on a surface of the sheet, one pocket near each of the lateral edges, and extend from the proximal to the distal edges. The pockets are formed to contain a removable, rigid support splint of metal or plastic formed with a curvature to conform to the user's wrist and palm. The splint is inserted in one of the pockets depending on which wrist the slit sleeve is being worn. One of the pockets is covered with hook and loop fastener material cooperable with the fastener material on the plurality of fastening tabs. The fastening tabs are attached the opposite lateral edge.

10 Claims, 2 Drawing Sheets

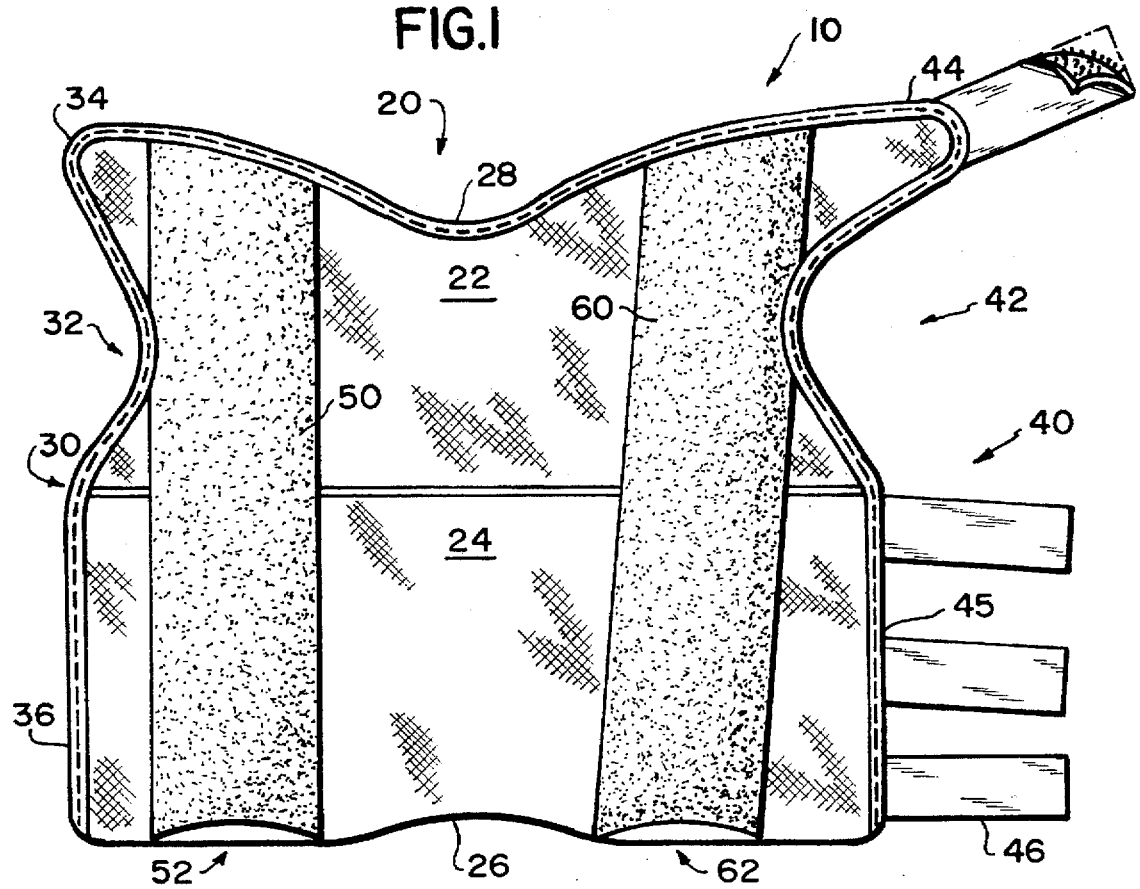

5,728,059

SLIT SLEEVE WRIST SUPPORT

FIELD OF THE INVENTION

The present invention relates to an ambidextrous wrist support having a rigid splint.

BACKGROUND AND SUMMARY OF THE INVENTION

A number of wrist support devices proposed in the art include sleeves, wraps, and other devices, however, various problems relating to fit, adjustability, and adaptability for ambidextrous supports have not been satisfactorily overcome.

The present invention, generally, provides a wrist support for use on either the right or the left hand, that overcomes the problems in the art.

The wrist support of the invention is formed as a slit sleeve that may be wrapped and fastened about the wrist, which permits adjustment of the fit and pressure applied to the wrist.

The wrist support of the present invention includes a sheet of flexible material formed with pockets for a rigid splint. The split sleeve form of the wrist support permits the user to position the splint on the palm at an optimal location for needed support and for comfort. Thumb spaces formed at opposing lateral edges which permits the user to position the thumb space and fastening elements for optimal comfort and support.

The slit sleeve according to the invention includes a sheet of elastic fabric that is wrapped around the wrist and hand and fastened with hooked loop fastening materials. The sheet has a proximal edge positionable around the arm and a distal edge positionable at the hand near the fingers. Each of the lateral edges is formed with a inward curved space near the distal end to accommodate the user's thumb. The curvature at each lateral edge distal of the thumb space defines opposed, laterally extending thumb tabs at the distal end of the sheet.

Two elongated pockets are sewn on a surface of the sheet, one pocket near each of the lateral edges, and extend from the proximal to the distal edges. The pockets are formed to contain a removable, rigid support splint of metal or plastic formed with a curvature to conform to the user's wrist and palm. The splint is inserted in one of the pockets depending on which wrist the slit sleeve is being worn. One of the pockets is covered with a hook and loop fastening material, and a plurality of fastening tabs, having a complementary hook and loop material, are attached to the opposite lateral edge.

The slit sleeve is placed on the hand with the pocket carrying the splint on the palm, and the thumb positioned in the adjacent curved space. The thumb tabs are positioned between the thumb and first finger and the free lateral edge is wrapped around the hand and fastened with the tabs.

BRIEF DESCRIPTION OF THE DRAWING FIGURES

The present invention can be further understood with reference to the following description in conjunction with the appended drawings, wherein like elements are provided with the same reference numerals. In the drawings:

FIG. 1 is a top view of a wrist support in accordance with the present invention;

FIG. 2 is a front view of a splint for the wrist support of FIG. 1;

FIG. 3 is a right side view of the splint of FIG. 2;

DETAILED DESCRIPTION OF PREFERRED EMBODIMENTS

Figure 4:
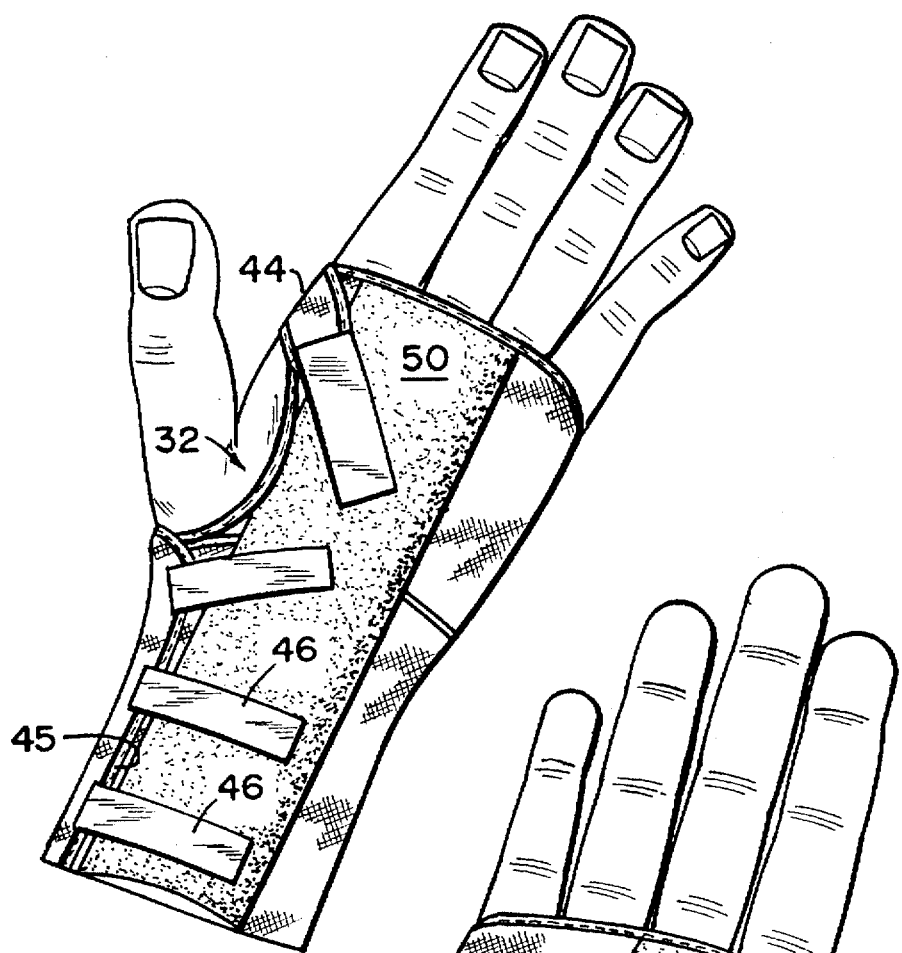
FIG. 4 is a dorsal view of a right hand with the wrist support of FIG. 1.

The slit sleeve wrist support 10, shown in FIG. 1, is formed of a sheet 20 of flexible, elastic material having a generally rectangular shape. The sheet 20 may comprise at least two separate parts 22, 24, as shown. By selection of the length and curvature of the attached edges, a curvature in the plane of the sheet 20 may be provided for the completed sheet which may provide a fit better conforming to the user's hand and wrist.

The wrist support 10 has a proximal edge 26 that is positionable around an arm near the wrist, and a distal edge 28 that is positionable about the hand near the fingers. As may be seen, the proximal edge 26 follows a substantially straight line. The distal edge 28 is formed with a concave curvature through a middle portion, which facilitates fitting the brace on a user's hand. The middle portion of the distal edge is positionable adjacent to the fifth finger, and the palm is typically shorter at the fifth finger side than on the thumb side.

The sheet is made sufficiently long from proximal 26 the distal edge 28 so that the wrist support 10 extends across the user's palm and on the wrist so that the wrist support, when in position, immobilizes the wrist when a splint is provided, as further described below.

The sheet 20 is formed of a material that is thin, flexible and elastic, which allows it to conform to a user's wrist and hand, and apply pressure to the wrist and hand by suitably tensioning the sheet. The material may be of the type that is elastic in one direction only, in which case the sheet 20 is oriented to be elastic in the lateral direction. Alternatively, the sheet 20 may comprise a neoprene rubber or other similar material.

The wrist support has opposite lateral edges 30, 40 extending between the proximal and distal edges. A distal portion of each of the lateral edges 30, 40 is shaped with a concave curvature. The curvature defines opposed spaces or gaps to accommodate the base of the user's thumb, and tabs 34, 44 which are positionable between the thumb and first finger, as more fully described below. A proximal portion 36, 45 of each of the lateral edges 30, 40 is substantially straight.

Two longitudinally extending pockets 50, 60 are fastened on the sheet 20, one adjacent to each of the gaps 32, 42. The pockets 50, 60 each have an opening 52, 62 at the proximal end of the wrist brace 10 to allow the selective insertion and removal of a splint 80, which is illustrated in FIGS. 2 and 3. The pockets 50, 60 are located on a surface of the wrist brace 10 opposite to a surface that is in contact with the user's hand when the wrist brace is worn.

A plurality of fastening straps 46 are attached to the wrist brace along the lateral edge 40. The straps 46 and the pocket 50 at the opposing lateral edge 30 are provided with complementing hook and loop type fasteners, for example, so that the straps 46 may be easily fastened and adjustably positioned on the pocket 50.

FIGS. 2 and 3 illustrate a splint 80 in accordance with the present invention. The splint 80 is an elongated member, preferably of a thin, rigid material such as metal or plastic. The splint material may also be chosen to provide some flexibility to permit limited flexion and extension movement of the user's wrist. The longitudinal and lateral dimensions of the splint are selected so that it fits in either of the pockets 50, 60 to extend substantially from the proximal end 26 to the distal end 28 of the wrist support 10. The splint 80 is shaped with a curvature, as shown in the side view of FIG. 3, to conform to the palm and wrist of the user to maintain the hand slightly in extension relative to the wrist. The splint 80 may be positioned in either of the pockets 50, 60 for either the right or left hand of the user, as more fully described below.

Figure 5:
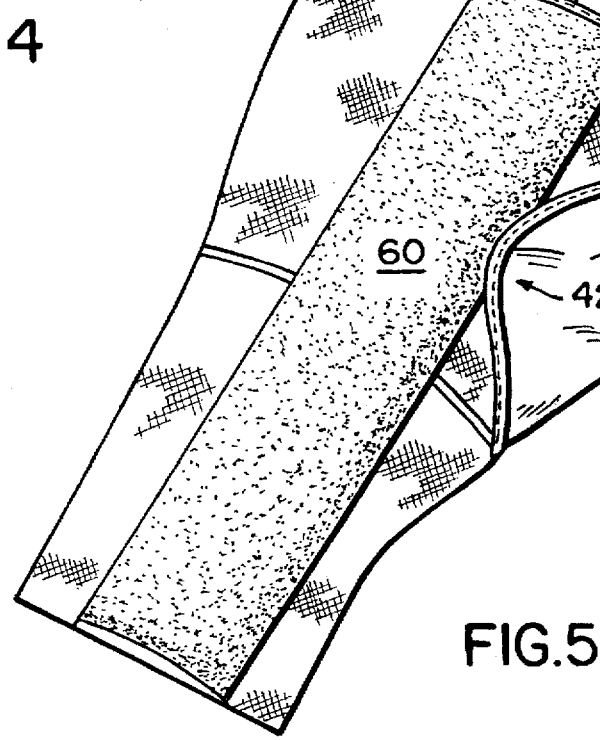
FIG. 5 is a palm side view of the right hand and wrist support of FIG. 4.

FIGS. 4 and 5 illustrate the wrist support 10 positioned on a right hand. Although shown and described for the right hand, it is understood that the wrist support 10 is correspondingly positionable on a left hand. FIG. 4 shows a dorsal view of the hand and FIG. 5 shows the palm side of the hand. The splint 80 is positioned (although not visible) in the pocket 60 shown in the palm side view of FIG. 5.

To put the wrist support 10 on the wrist, the wrist support 10 is positioned on the palm of the hand with the splint holding pocket 60 in the desired position on the palm and wrist, and the thumb positioned in the appropriate gap 42. The user then wraps the wrist support 10 around the hand and wrist so that the opposing gap 32 is adjacent the thumb, and the tabs 34 and 44 and proximal lateral edges 36, 45 overlap as required to provide a secure and comfortable fit on the hand. The size of the space for the thumb between the tabs 34, 44 and the proximal portions 36, 45 may be adjusted for optimal fit and comfort by the relative positioning, that is, more or less overlapping of the lateral edges.

Because the pockets 50, 60 for the splint are positioned adjacent to the free lateral edges 30, 40, the position of the splint 80 relative to the thumb is also adjustable to provide optimal desired support for the wrist and thumb.

The foregoing has described the preferred principles, embodiments and modes of operation of the present invention; however, the invention should not be construed as limited to the particular embodiments discussed. Instead, the above-described embodiments should be regarded as illustrative rather than restrictive, and it should be appreciated that variations, changes and equivalents may be made by others without departing from the scope of the present invention as defined by the following claims.

What is claimed is:

1. An ambidextrous slit sleeve wrist support comprising:
   (A) a sheet of flexible, elastic material having a distal edge, a proximal edge, and opposite lateral edges, said lateral edges being shaped in a distal end portion with oppositely located arcuate portions defining concave gaps adapted to receive a thumb;
   (B) a first elongated pocket adapted to receive a selectably positionable splint, said first elongated pocket being positioned on a first surface of the sheet extending substantially from the proximal edge to the distal edge adjacent to a first of said lateral edges, said first elongated pocket having an opening at the proximal edge for receiving said selectably positionable splint;
   (C) a second elongated pocket also adapted to receive said selectably positionable splint, said second elongated pocket being positioned on the first surface of the sheet extending substantially from the proximal edge to the distal edge adjacent to a second of said lateral edges, said second elongated pocket having an opening at the proximal edge for receiving said selectably positionable splint;
   (D) a plurality of fastening straps extending laterally from the second lateral edge, said fastening straps being fastenable to an outer surface of the first elongated pocket; and
   (E) a splint selectably positionable in one of said elongated pockets; and
   wherein said splint is positioned in said first elongated pocket, said sheet of flexible, elastic material is wrapped around the wrist of one hand of a user so that the splint becomes associated with the thumb of said hand of said user, and the plurality of fastening straps is fastened to said outer surface of said first elongated pocket to form a slit sleeve wrist support on said hand of said user; or
   said splint is positioned in said second elongated pocket, said sheet of flexible elastic material is wrapped around the wrist of the opposite hand of said user so that the splint becomes associated with the thumb of said opposite hand of said user, and the plurality of fastening strips is fastened to said outer surface of said first elongated pocket to form a slit sleeve wrist support on said opposite hand of said user.

2. The wrist support as claimed in claim 1, wherein the splint is shaped to conform substantially with a palm and wrist to position the palm in extension relative to the wrist.

3. The wrist support as claimed in claim 1, wherein the first elongated pocket on the outer surface and the fastening straps have cooperating hook and loop fastening material.

4. The wrist support as claimed in claim 1, wherein the distal edge is formed as a concave, arcuate edge.

5. The wrist support as claimed in claim 1, wherein each of the gaps on the lateral edges defines a tab adjacent to the distal edge positionable between a thumb and forefinger, a fastening strap extending laterally from the tab on the second lateral edge.

6. The wrist support as claimed in claim 5, wherein the distal edge is formed as a concave, arcuate edge.

7. The wrist support as claimed in claim 6, wherein the wrist support is positionable on a hand with the arcuate distal edge adjacent to a fifth finger and the tabs of the lateral edges overlap in a region between a thumb and forefinger, a proximal portion of the lateral edges being positionable around a wrist and base of a thumb.

8. The wrist support as claimed in claim 1, wherein the sheet material is flexible in the proximal to distal direction and the lateral direction, and is flexible and elastic in the lateral direction.

9. The wrist support as claimed in claim 1, wherein the splint is formed of a rigid material.

10. The wrist support as claimed in claim 1, wherein the sheet has a length from proximal to distal edge sufficient to extend from an arm across a wrist to adjacent to a user's fingers so that the wrist support immobilizes the user's wrist.

* * * * *